United States Patent [19]

Rouy et al.

[11] Patent Number: 4,518,781
[45] Date of Patent: May 21, 1985

[54] PROCESS FOR THE PREPARATION OF 3-HYDROXYMETHYL-6-CHLOROBENZOXAZOLONE

[75] Inventors: Noël Rouy, Yérres; Francois Dewilde, Thiais, both of France

[73] Assignee: Rhone-Poulenc Agrochimie, Lyon, France

[21] Appl. No.: 556,565

[22] Filed: Nov. 30, 1983

Related U.S. Application Data

[62] Division of Ser. No. 242,538, Mar. 11, 1981, Pat. No. 4,435,557.

[30] Foreign Application Priority Data

Mar. 27, 1980 [FR] France ................ 80 07262

[51] Int. Cl.$^3$ ............................. C07D 498/04
[52] U.S. Cl. ................................. 548/221
[58] Field of Search ....................... 548/221

[56] References Cited

U.S. PATENT DOCUMENTS 3,081,170  3/1963  Rauch et al. .............. 548/221
3,161,520 12/1964  Rauch et al. .............. 548/221
3,682,933  8/1972  Engel ......................... 548/221
3,996,279 12/1976  Schlager .................... 564/390

FOREIGN PATENT DOCUMENTS 37352  10/1981  European Pat. Off. ......... 221/
245111  1/1968  U.S.S.R. ...................... 548/221

OTHER PUBLICATIONS

Zinner, H. et al., (I), Chem. Ber., 89 (9), pp. 2131–2136, (1956).
Zinner, H. et al., (II), Chem. Ber., 90, pp. 2246–2253, (1957).
Sexton, W. A. et al., J.C.S., p. 1717, (1948).

*Primary Examiner*—Donald G. Daus
*Assistant Examiner*—S. A. Gibson
*Attorney, Agent, or Firm*—Burns, Doane, Swecker & Mathis

[57] ABSTRACT

Process for the preparation of optionally hydroxymethylated 6-chlorobenzoxazolone, which consists in chlorinating and, if appropriate, hydroxymethylating benzoxazolone in a mixture of water and dioxane.

22 Claims, No Drawings

PROCESS FOR THE PREPARATION OF 3-HYDROXYMETHYL-6-CHLOROBENZOXAZOLONE

CROSS-REFERENCE TO RELATED APPLICATION

This application is a division of application Ser. No. 242,538, filed Mar. 11, 1981, now U.S. Pat. No. 4,435,557.

The present invention relates to a process for the preparation of chlorinated derivatives of benzoxazolone, which can be used, in particular, as intermediates in the preparation of insecticides.

More precisely, the invention relates to the preparation of derivatives of the 6-chlorobenzoxazolone type of the formula

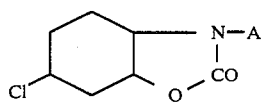  (I)

in which A represents a hydrogen atom or a hydroxymethyl group.

One object of the invention is to make it possible to obtain derivatives of the formula (I) with good yields using benzoxalone as the starting material or reactant.

Benzoxazolone is understood as meaning the product of the formula

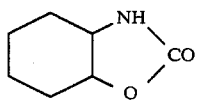

This product is sometimes referred to as benzoxazolinone, especially in the English language.

Another object of the invention is to make it possible to use moist benzoxazolone, which is a form of benzoxazolone obtained conveniently and economically on an industrial scale.

Russian Pat. No. 245,111 has already described the chlorination of benzoxazolone in chlorinated alkanes or alkenes, such as tetrachloroethane.

It is also known that benzoxazolone is converted to 3-hydroxymethylbenzoxazolone by reaction with formaldehyde in aqueous solution [Zinner et al., Ber., 89, 2,135 (1956)].

However, these various processes are not satisfactory for various reasons related, in particular, to the purity of the products obtained or to the limited degree of conversion of the reaction.

One object of the invention is to provide a process for the preparation of derivatives of the formula (I) which does not have the disadvantages of the known processes.

Another object of the invention is to provide a process for the preparation of derivatives of the formula (I) which, as far as possible, avoids the formation of abnormally chlorinated products, such as the derivatives polychlorinated on the aromatic nucleus.

Another object of the invention is to facilitate the separation and the purification of the products of the formula (I) obtained at the end of the reaction.

Another object of the invention is to provide a process for the preparation of products of the formula (I) which makes it possible, at the end of the reaction, easily to recover the solvents which may have been used during the reaction.

Another object of the invention is to provide a means of conveniently linking various operations necessary for obtaining certain intermediates for the preparation of phosalone.

It has now been found that these objects can be achieved by virtue of the process forming the subject of the present invention.

This process according to the invention comprises reacting benzoxazolone with chlorine in the presence of water and dioxane.

The mixture of water+dioxane used in the process of the invention generally comprises between 20 and 80% by weight of dioxane and preferably more than 50% of dioxane.

The amount of benzoxazolone used in the reaction is generally between 50 and 500 g/liter (grams per liter of reaction mixture) and preferably between 150 g/liter and 400 g/liter.

The chlorine is generally added by gradual introduction into the reaction medium, where it dissolves and/or reacts rapidly; the reaction time can vary very widely, but, for economic reasons, it is generally between 1 hour and 15 hours and preferably between 2 and 10 hours.

The reaction temperature is generally between −20° C. and +90° C. and preferably between 40° and 80° C.

The main reaction product obtained in accordance with the process which has now been described is 6-chlorobenzoxazolone of the formula

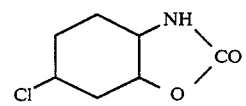

The reaction is advantageously continued until a maximum yield of 6-chlorobenzoxazolone has been obtained; the course of the reaction can be followed by any means which is in itself known, e.g. potentiometry. The presence of an aqueous reaction medium is advantageous for the very reason that it makes it possible conveniently to follow the course of the reaction by potentiometry.

It is also possible to adapt the amount of chlorine added so as to obtain this maximum yield of 6-chlorobenzoxazolone. The amount of chlorine added is advantageously close to the stoichiometric amount; it is generally between 1 and 1.1 mols/mol (i.e. mols of chlorine per mol of benzoxazolone used) and preferably between 1.03 and 1.07 mols/mol.

Hydrogen chloride is formed during the reaction and dissolves at least partially in the reaction medium, but can also be evolved in the gaseous state.

At the end of the reaction, the reaction mixture is advantageously neutralized with a basic agent, e.g. a hydroxide or carbonate of an alkali metal or alkaline earth metal, preferably of sodium or potassium.

Very frequently, the presence of the different reaction and neutralization products causes salting out, i.e. separation of the reaction medium into two liquid phases, the one being essentially organic and the other essentially aqueous.

According to a first variant of the invention, the 6-chlorobenzoxazolone is isolated from the reaction medium by any means which is in itself known, e.g. by crystallization.

According to a convenient embodiment of the invention, the yield and the purity of the 6-chlorobenzoxazolone obtained can be adjusted by modifying the conditions of crystallization, in particular the water/dioxane ratio and the temperature during this crystallization and the subsequent filtration.

According to another variant of the process of the invention, the 6-chlorobenzoxazolone is reacted with formaldehyde to form 3-hydroxymethyl-6-chlorobenzoxazolone, or in other words the product of the formula (I) in which A represents a hydroxymethyl radical. According to an especially advantageous embodiment, the 6-chlorobenzoxazolone is used in the form of the organic layer obtained at the end of the previous reaction, which makes it possible to avoid any crystallization or other form of isolation of the 6-chlorobenzoxazolone.

The formaldehyde used can be in the form of paraformaldehyde or more simply in the form of an aqueous solution (formol).

The reaction is carried out at between 20° and 100° C. and preferably between 60° and 90° C.; the formaldehyde is advantageously used in excess, relative to the 6-chlorobenzoxazolone. The molar ratio $$\frac{formaldehyde}{6\text{-chlorobenzoxazolone}}$$

is generally between 0.8 and 2 and preferably between 1 and 1.3.

The concentration of 6-chlorobenzoxazolone used in the reaction is within the same limits as those indicated for the benzoxazolone in the previous reaction step; the same applies to the water/dioxane ratio.

At the end of the reaction, the 3-hydroxymethyl-6-chlorobenzoxazolone is isolated by any means which is in itself known, e.g. by crystallization. As in the previous step, it is possible to adjust the yield and the degree of purity of the 3-hydroxymethyl-6-chlorobenzoxazolone by modifying the water/dioxane ratio and the temperature at which the crystallization/filtration operations are carried out.

The 3-hydroxymethyl-6-chlorobenzoxazlone can be converted to 3-chloromethyl-6-chlorobenzoxazolone with the aid of known chlorinating agents (PCl$_3$, SOCl$_2$ and the like), and the 3-chloromethyl-6-chlorobenzoxazolone can itself be used to produce insecticidal products (phosalone) in accordance with known processes.

The following examples, which are given without implying a limitation, illustrate the invention and show how it can be put into effect.

EXAMPLE 1

Water (335 g), dioxane (457 g) and benzoxazolone (270 g) are introduced into a 2 liter reactor.

The medium is heated to a temperature of 40° C. and chlorine is injected into this medium at a rate of 10 liters/hour, by means of a glass tube, until an amount of 147 g has been absorbed by the reaction medium (reaction followed by potentiometry).

The reaction medium is neutralized with an aqueous sodium hydroxide solution of 30% strength by weight (246 g). The temperature is then raised to 85° C. and salting out takes place; the upper organic phase, which contains mainly dioxane and 6-chlorobenzoxazolone, is separated off by decantation. Water (250 g) is added thereto and the medium is heated to 80° C., which makes it homogeneous, and cooled to 20° C., which causes the 6-chlorobenzoxazolone to crystallize. By filtration, the latter is obtained with a yield of 85.7% (relative to the benzoxazolone used) and a degree of purity of 99%.

EXAMPLE 2

Example 1 is repeated up to the salting-out step. The organic phase is separated off by decantation. A 30% strength by weight aqueous sodium hydroxide solution (about 1 cc) is added to this organic phase so that the pH becomes equal to 4.5; an aqueous formaldehyde solution of 30% strength by weight (202 cc) is then added. The mixture is heated at 65° C. for half an hour.

At the end of the reaction, water (235 g) is added and the mixture is cooled, which causes the 3-hydroxymethyl-6-chlorobenzoxazolone to crystallize, the latter thus being obtained with a yield of 83% (relative to the benzoxazolone initially used at the start of Example 1) and a degree of purity of 99.5%.

We claim:

1. A process for the preparation of 3-hydroxymethyl-6-chlorobenzoxazolone which comprises reacting 6-chlorobenzoxazolone in organic solution with formaldehyde in the presence of water and dioxane, the 6-chlorobenzoxazolone having been prepared by reacting benzoxazolone with molecular chlorine in the presence of water and dioxane wherein said organic solution being 6-chlorobenzoxazolone and dioxane.

2. A process according to claim 1, wherein the mixture of water and dioxane for each reaction comprises between 20 and 80% of dioxane.

3. A process according to claim 2, wherein the mixture of water and dioxane for each reaction comprises more than 50% of dioxane.

4. A process according to claim 1, wherein the formaldehyde is in aqueous solution.

5. A process according to claim 2, wherein the formaldehyde is in aqueous solution.

6. A process according to claim 3, wherein the formaldehyde is in aqueous solution.

7. A process according to claim 1, wherein the molar ratio of formaldehyde/6-chlorobenzoxazolone is between 0.8 and 2.

8. A process according to claim 2, wherein the molar ratio of formaldehyde/6-chlorobenzoxazolone is between 0.8 and 2.

9. A process according to claim 4, wherein the molar ratio of formaldehyde/6-chlorobenzoxazolone is between 0.8 and 2.

10. A process according to claim 7, wherein the molar ratio is between 1 and 1.3.

11. A process according to claim 8, wherein the molar ratio is between 1 and 1.3.

12. A process according to claim 9, wherein the molar ratio is between 1 and 1.3.

13. A process according to claim 1, wherein the amount of 6-chlorobenzoxazolone used is between 50 and 500 g/liter of reaction mixture and the reaction temperature is between 20° and 100° C.

14. A process according to claim 2, wherein the amount of 6-chlorobenzoxazolone used is between 50 and 500 g/liter of reaction mixture and the reaction temperature is between 20° and 100° C.

15. A process according to claim 4, wherein the amount of 6-chlorobenzoxazolone used is between 50 and 500 g/liter of reaction mixture and the reaction temperature is between 20° and 100° C.

16. A process according to claim 7, wherein the amount of 6-chlorobenzoxazolone used is between 50 and 500 g/liter of reaction mixture and the reaction temperature is between 20° and 100° C.

17. A process according to claim 10, wherein the amount of 6-chlorobenzoxazolone used is between 50 and 500 g/liter of reaction mixture and the reaction temperature is between 20° and 100° C.

18. A process according to claim 13 wherein the amount of 6-chlorobenzoxazolone used is between 150 and 400 g/liter and the reaction temperature is between 60° and 90° C.

19. A process according to claim 14 wherein the amount of 6-chlorobenzoxazolone used is between 150 and 400 g/liter and the reaction temperature is between 60° and 90° C.

20. A process according to claim 15 wherein the amount of 6-chlorobenzoxazolone used is between 150 and 400 g/liter and the reaction temperature is between 60° and 90° C.

21. A process according to claim 16 wherein the amount of 6-chlorobenzoxazolone used is between 150 and 400 g/liter and the reaction temperature is between 60° and 90° C.

22. A process according to claim 19 wherein the amount of 6-chlorobenzoxazolone used is between 150 and 400 g/liter and the reaction temperature is between 60° and 90° C.

* * * * *